United States Patent [19]

Starks

[11] 4,080,824
[45] Mar. 28, 1978

[54] TEST SPECIMEN GRIP ASSEMBLY

[76] Inventor: Emmett A. Starks, 988 Chatham Pl., Rocky River, Ohio 44116

[21] Appl. No.: 732,015

[22] Filed: Oct. 13, 1976

[51] Int. Cl.² .............................................. G01N 3/04
[52] U.S. Cl. ..................................................... 73/103
[58] Field of Search ............................ 73/103, 95, 95.5; 269/217

[56] References Cited

U.S. PATENT DOCUMENTS

| | | | |
|---|---|---|---|
| 1,122,289 | 12/1914 | Loveland | 73/103 |
| 1,341,431 | 5/1920 | Morrow | 73/103 |
| 3,005,336 | 10/1961 | Wyman | 73/103 |
| 3,107,524 | 10/1963 | O'Connor | 73/103 |
| 3,138,952 | 6/1964 | Dobbin | 73/95 |
| 3,344,662 | 10/1967 | Pruett | 73/103 |

Primary Examiner—Anthony V. Ciarlante
Attorney, Agent, or Firm—Donnelly, Maky, Renner & Otto

[57] ABSTRACT

A test specimen grip assembly for holding a metallurgical test specimen in a test apparatus operative to apply tensile force to the specimen. The grip assembly includes plural tapered inserts which apply to the specimen a radial wedge gripping force that increases as the tensile force is increased. The inserts are received in a holder mechanism including a cup-shape holder within which a hemispherical ring is rotatably seated for alignment purposes, and a frusto-conical opening is provided in the ring for receiving the inserts. In an alternate embodiment an adaptor is connected to the specimen to facilitate securing the latter in the test apparatus.

18 Claims, 16 Drawing Figures

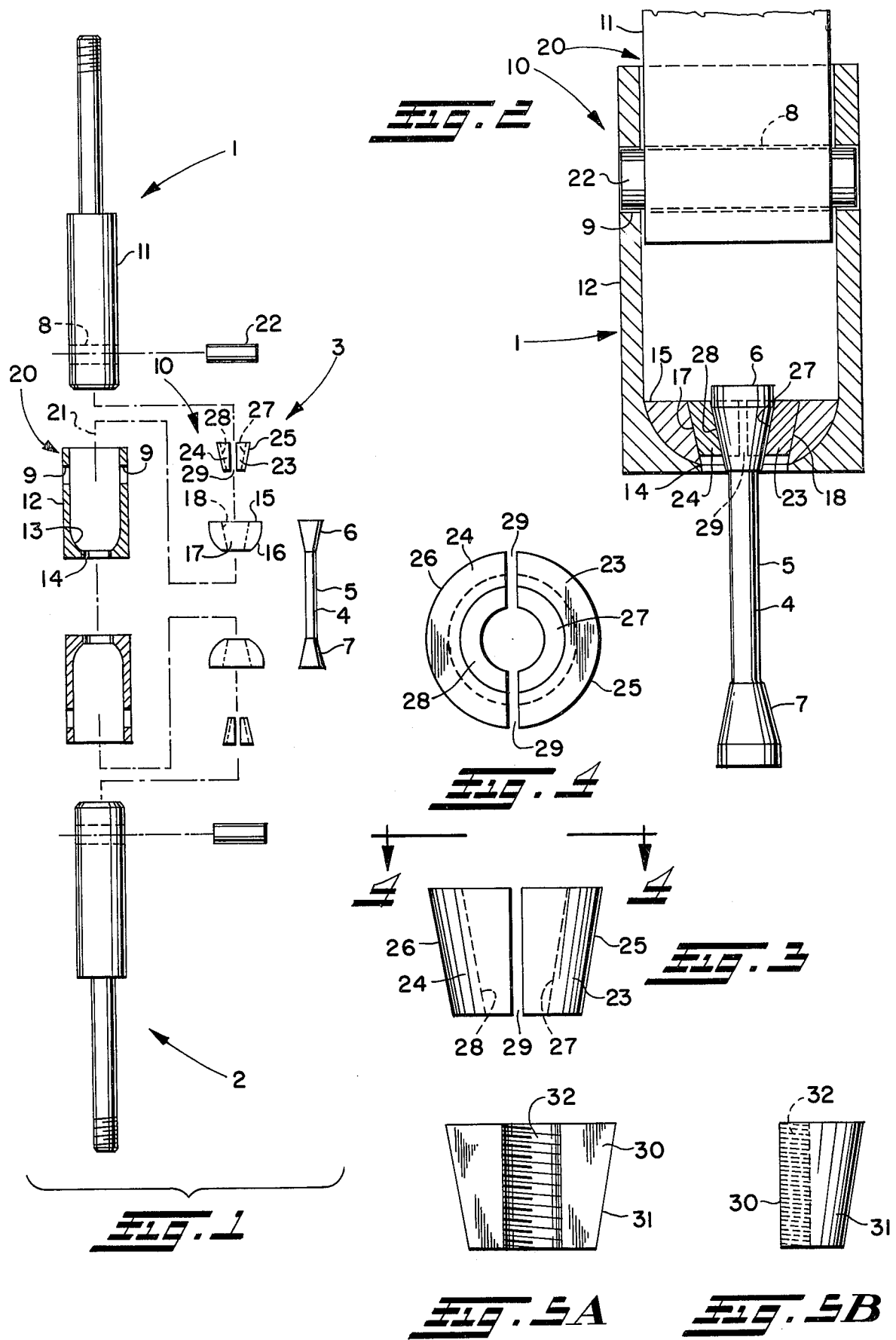

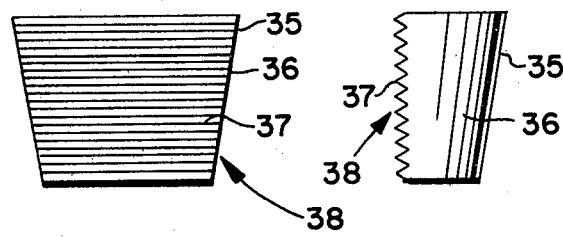
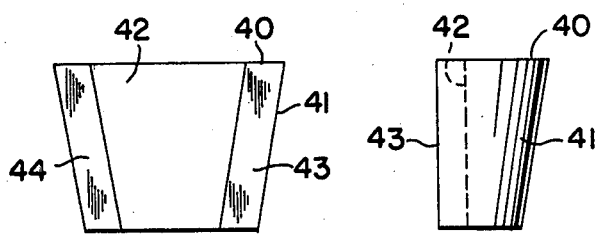
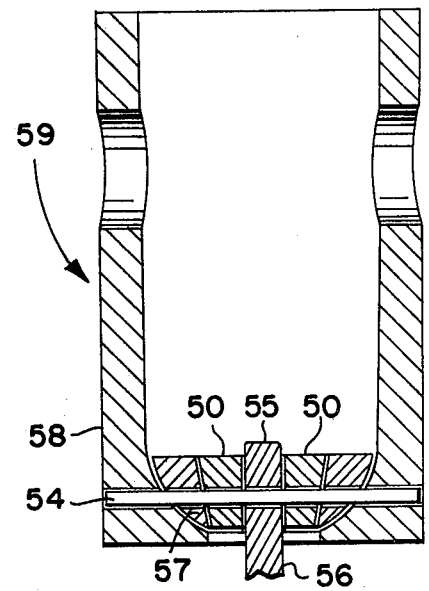
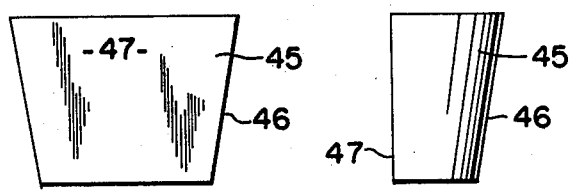
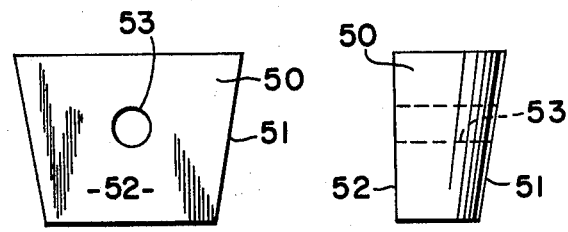
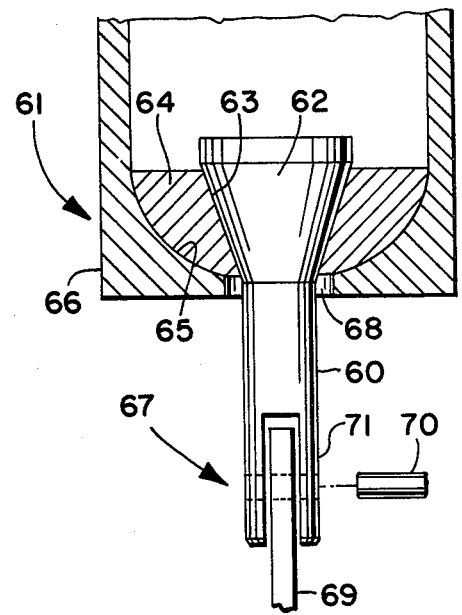

TEST SPECIMEN GRIP ASSEMBLY

BACKGROUND OF THE INVENTION

The present invention relates to a test specimen grip assembly and, more particularly, to a load train grip assembly for holding a metallurgical specimen in a test apparatus for performing tensile, creep/stress or like analyses.

A typical metallurgical test specimen is disclosed, for example, in U.S. Pat. No. 3,107,522, and includes a main body generally of linear or axial extent with frusto-conical end portions to facilitate gripping of the same in a tension testing machine. The end portions are gripped in respective cylindrical holders by work holding jaws formed by a pair of pins inserted through respective bores in the holder, the pins being rotatable in their bores to facilitate self-centering or self-alignment of the specimen in the axial direction as tensile force is applied. In U.S. Pat. No. 3,107,524 a hemispherical seat in a cup holder receives a split hemispherical bit that forms a self-aligning jaw.

Tension or like testing machines are, of course, known in which tensile force is applied to a specimen under ambient, heated, or cooled conditions to effect metallurgical or like analyses of the specimen.

Although prior gripping devices provide for some self-alignment or self-centering of a specimen during tensile or like testing thereof, at the conclusion of such testing it is often-times difficult and time consuming to separate the respective parts of such prior gripping devices and the specimen gripped thereby because of inelastic shape changes of those parts. Also, in many instances some of the grip assembly parts must be replaced before the device can be reused again or after a few times, which greatly adds to the overall cost of the device and restricts its usefulness.

SUMMARY OF THE INVENTION

The grip assembly of the present invention facilitates disassembly after completion of a test as well as assembly prior to such test. Also, such grip assembly grips the specimen securely during testing, and aids in self-alignment of the specimen during testing. In the preferred embodiment two similar grip assemblies, each being part of a respective holder mechanism, which is in turn part of a load train grip assembly of the test apparatus, grip the opposite ends of the specimen. However, it will be appreciated that, if desired, one of the two holder mechanisms may be of another type.

In the preferred form of the invention, the holder mechanism includes a cup-shape holder with a hemispherical seat on which a hemispherical ring is placed. The ring has a tapered opening, preferably of frusto-conical shape, therethrough forming a tapered seat. A plurality of inserts, each having a tapered, preferably generally frusto-conical like shape outer wall surface that conforms to the tapered seat and an inner wall surface to grip the specimen, are movably placed in the ring opening to engage both the ring and the specimen. The test apparatus applies tensile force to the specimen via the holder mechanism, and as the tensile force or pull is increased, the radial gripping thrust or force of the inserts on the specimen also increases due to the wedging action of the inserts in the ring opening. As a result, the specimen is securely held during the testing operation. Also during the testing operation the hemispherical ring in cooperation with the hemispherical seat on the cup-shape holder aid in self-alignment of the entire load train grip assembly, including the specimen, to provide more even distribution of the tensile forces in the latter. Following the testing operation, disassembly is also greatly facilitated by the relatively easily removed plural inserts.

In another embodiment an adaptor, which effectively extends the length of the specimen, may be provided which is gripped at one end in the tapered seat of the hemispherical ring and is easily coupled and uncoupled to the specimen at its other end.

The inserts may take various forms so as to present interior surfaces suitable for confronting and bearing against various shaped surfaces of the specimen end portions. If desired, to assure proper positioning of the specimen and the holder mechanism, a pin may be inserted through respective aligned bores in the various elements of the holder mechanism and specimen.

With the foregoing in mind it is a primary object of this invention to hold a specimen securely in a test apparatus or the like and, particularly, to hold a metallurgical specimen in a test instrument that applies tensile forces to the specimen.

Another object is to provide a radial gripping thrust or force to wedgingly grip a specimen and, particularly, to increase such thrust as tensile pull on the specimen is increased.

An additional object is to facilitate assembly and, more importantly, disassembly of a test specimen grip assembly.

A further object is to aid in self-aligning a metallurgical specimen during tensile testing or the like.

Still another object is to combine self-alignment and strong gripping force features for a specimen in a tensile test assembly or the like.

Still an additional object is to increase the life of parts in a test specimen grip assembly.

A further object is to reduce problems, such as deformation, fatique, and the like, caused by heat applied directly or indirectly to a load train grip assembly where at least the test specimen is heated.

These and other objects and advantages of the present invention will become more apparent as the following description proceeds.

To the accomplishment of the foregoing and related ends, the invention, then, comprises the features hereinafter fully described in the specification and particularly pointed out in the claims, the following description and the annexed drawings setting forth in detail certain illustrative embodiments of the invention, these being indicative, however, of but several of the various ways in which the principles of the invention may be employed.

BRIEF DESCRIPTION OF THE DRAWINGS

In the annexed drawings:

FIG. 1 is an exploded view, partly in section, of a load train grip assembly in accordance with the invention;

FIG. 2 is a partial front sectional view of one assembled holder mechanism of the load train grip assembly of FIG. 1;

FIG. 3 is an enlarged side view of a pair of one form of tapered inserts that may be utilized in the holder mechanism of FIGS. 1 and 2;

FIG. 4 is a top view of the tapered inserts of FIG. 3 looking in the direction of the arrows 4—4;

FIGS. 5A and 5B are front and side views, respectively, of a threaded tapered insert;

FIGS. 6A and 6B are front and side views, respectively, of a serrated tapered insert;

FIGS. 7A and 7B are front and side views, respectively, of a tapered insert having a flat tapered interior gripping surface;

FIGS. 8A and 8B are front and side views, respectively, of a plane or flat tapered insert;

FIGS. 9A and 9B are front and side views, respectively, of a tapered insert with a transverse bore therethrough for pinning to a test specimen;

FIG. 10 is a partial sectional view of an assembled holder mechanism using a pinned tapered insert arrangement in accordance with the invention; and FIG. 11 is a partial sectional view of a modified holder mechanism in accordance with the present invention employing an adaptor extension.

DESCRIPTION OF THE PREFERRED EMBODIMENTS

In referring now more particularly to the drawings, wherein like reference numerals designate like or similar parts in the several figures, the several embodiments of the test specimen grip assembly in accordance with the invention will be described with reference to a holder mechanism for holding a metallurgical test specimen as part of a load train grip assembly in a testing apparatus which is operative to apply tensile forces to the specimen for conventional testing purposes, such as, for example, to determine the tensile force at which the specimen fails.

FIG. 1 shows the several parts of the two halves 1, 2 of a load train grip assembly 3 in disassembled, exploded form relative to a conventional metallurgical test specimen 4. As illustrated, the specimen 4 is of the elongate type having an elongate central body 5 and a pair of opposite end portions 6, 7, which are preferably of frusto-conical shape. Both halves 1 and 2 of the load train grip assembly 3 are preferably similarly formed and each includes a holder mechanism 10 intended to grip the specimen 4 and a rod 11 that is coupled in the test apparatus, not shown, to apply a tensile or pulling force to the specimen via the holder mechanism.

The holder mechanism 10 comprises a cup-shape holder 12 that has an hemispherical seat 13 formed at one interior end thereof, such seat generally circumscribing a through opening 14 of sufficient diameter to accept the enlarged end portion 6 of the specimen 4. An hemispherical ring 15 having an exterior surface 16 of approximately the same size and shape as that of the hemispherical seat 13 is adapted to be relatively movably positioned on such seat in the manner illustrated, for example, in FIG. 2. An axial opening 17 through the ring 15 has an angularly tapered interior wall, which is preferably of generally frusto-conical shape, that defines a tapered seat 18 within the ring. The ring 15 is preferably continuous about its circumference to facilitate insertion through the open end 20 of the holder 12 and positioning on the hemispherical seat 13 such that the holder opening 14 and the ring opening 17 are generally axially aligned with respect to the linear axis 21 shown in phantom in FIG. 1 along which the tensile force is normally applied by the test apparatus. The solid ring 15 also helps to assure even distribution of force between the ring and holder 12. The rod 11 is removably connected to the holder 12 as by means of a pin 22 extending through aligned openings 8 and 9 in the respective parts.

A plurality of tapered wedge inserts 23, 24 are insertable into the ring opening 17 for sliding wedge contact on the tapered seat 18 to facilitate gripping of the end portion 6 of the specimen 4. While the number of such inserts may vary, two inserts are preferably employed in each holder mechanism 10 with each insert being so formed to enable gripping of the specimen by application of a radial thrust wedging force thereto. The outer wall surfaces 25, 26 of the inserts 23, 24, like the tapered interior surface of the ring 15 that forms the tapered seat 18, are of generally frusto-conical shape and tapered to the same extent so that the inserts may be movably positioned along the tapered seat with a major extent of the abutting surfaces in direct engagement. Similarly, the inner or interior wall surfaces 27, 28 of the inserts 23, 24 are of a mating shape to that of the end portions 6, 7 of the specimen which is to be gripped thereby. In the form illustrated in FIGS. 1 through 4, the inner wall surfaces 27, 28 are of generally frusto-conical shape to mate with the correspondingly shaped end portions 6 of the specimen 4.

To assemble one half of the load train grip assembly 3, the wedge inserts 23, 24 may be placed around the specimen end portion 6 and positioned in the ring 15, after which the entire subassembly including the assembled inserts, specimen end portion and ring may be placed in the holder 12 in engagement with the hemispherical seat 13 with the openings 14 and 17 aligned as shown, for example, in the assembly of the half 1 in FIG. 2. When thus assembled, the holder mechanism 10 will grip the end portion 6 of the specimen 4 precluding its withdrawal from the holder 12. The assembled holder mechanism 10 thus forms the grip assembly for one end of the test specimen 4, and this assembly may be attached to the rod 11 which is inserted into the open end 20 of the holder 12 and attached thereto by the pin 22, as clearly shown in FIG. 2. The other half 2 of the load train grip assembly 3 may be assembled to grip the other end portion 7 of the test specimen 4 by placing the respective ring 15 in the holder 12 in engagement with the seat 13, and then inserting the specimen end portion 7 through the aligned openings 14 and 17 a sufficient amount to permit placing the inserts 23, 24 into the ring opening 17.

During a testing operation the test apparatus, not shown, applies a tensile force to the specimen 4 via the respective rods and holder mechanisms pulling the end portions 6 and 7 of the specimen in opposite directions. The respective inserts 23, 24 tend to be drawn toward the narrower end of the tapered seat 18 on which they are slidably positioned to wedge tightly against the specimen end portions thus assuring a strong grip force of the specimen which increases as the tensile force or pull is increased by the test apparatus. At the same time, the inserts 23, 24 in cooperation with the rings 15 aid in self-alignment of the load train grip assembly 3, including the specimen 4 to provide for more even distribution of the tensile forces in the latter. Sufficient clearance 29 must be provided between the adjacent sides of the inserts when in the assembled position shown in FIG. 2 so as not to interfere with the wedging of the inserts into tight gripping engagement with the specimen end portions as aforesaid.

After the testing operation has been concluded, the load train grip assembly 3 may be relatively easily disassembled simply by removing the pins 22 to disconnect the rods 11 from the holders 12 and moving the respective holders 12 toward each other. This will cause each specimen portion 6 and 7 to be urged into the respective holder to free the inserts 23, 24 allowing them to be easily removed which frees the specimen portions. If necessary, a relatively light blow may be applied to the specimen portion with a hammer or the like to free a gripped end portion of the specimen from the inserts.

While in the preferred form shown in FIGS. 1 through 4, the inner surfaces 27, 28 of the tapered inserts 23, 24 have a smooth frusto-conical shape to mate with the correspondingly shaped end portions 6, 7 of the specimen 4, it will be appreciated that other shapes and manner of connection with the specimen end portions may be provided depending on the shape of specimen being tested. In FIGS. 5A and 5B, for example, there is illustrated a threaded type of tapered insert 30. The outer wall surface 31 of the insert is of a generally frusto-conical shape to mate with the tapered seat 18 of the hemispherical ring 15, as before. However, the inner wall surface 32 is formed with screw threads, as illustrated, to grip a threaded end portion of a test specimen, not shown, to secure the same in the holder mechanism 10. Of course, a plurality of such threaded tapered inserts 30 would be placed in the ring opening 17 engaged with such threaded end portion of the specimen to grip the same. As tensile force is applied to the specimen, the plural inserts 30 are drawn toward each other in cooperation with the gripped specimen and the tapered seat 18 to wedgingly engage the specimen end portions thereby further increasing the radial gripping force on the threaded end portions of the specimen, as described above. Following the test, the holder mechanism using such threaded tapered inserts 30 may be disassembled in the manner previously described.

A serrated tapered insert 35 is illustrated in FIGS. 6A and 6B. Such insert has a tapered outer wall surface 36 of frusto-conical shape to fit in the tapered seat 18 of the ring 15 as described above and an inner wall surface 37 which is of a generally planar extent while having a plurality of serrations 38 formed therein. A plurality of such serrated tapered inserts 35 may be inserted into a ring opening 17 to grip a correspondingly shaped end portion of a test specimen generally in the manner described above. The serrated tapered inserts 35 may also be effectively used to grip the specimen end portions of various other shapes, such as, for example, those of enlarged shapes, as shown in FIG. 1, those of cylindrical shape, those of planar shape, sheet-like material, etc., the serrations 38 preferably being capable of strong biting engagement with such specimens.

Another form of insert 40 is shown in FIGS. 7A and 7B which has an outer wall surface 41 that is of generally frusto-conical shape to mate with the tapered seat 18 as described above. However, the inner wall surface 42 is generally planar and is bounded at opposite sides by lands 43, 44 so that in the plan view of FIG. 7A the inner wall surface 42 is of a planar trapezoidal shape. The interiorly tapered insert 40 is designed for use in gripping, for example, a specimen end portion that is of flattened triangular profile.

In FIGS. 8A and 8B a plain tapered insert 45 is illustrated having a tapered frusto-conical outer wall surface 46 and a planar inner wall surface 47. A plurality of such plain tapered inserts 45 may be employed in the above-described manner to grip a flat end portion of a test specimen, for example.

A modified tapered insert 50 is shown in FIGS. 9A and 9B and has a tapered frusto-conical shape outer wall surface 51 and a planar inner wall surface 52 similar to the plain tapered insert 45 described above. In addition, the tapered insert 50 has a transverse bore 53 to receive a pin 54, illustrated in FIG. 10, for coupling of a pair of such inserts 50, the end portion 55 of a test specimen 56, a hemispherical ring 57, and a cup-shape holder 58 through respective aligned bores in a modified holder mechanism 59. The pin connection of the embodiment illustrated in FIG. 10 facilitates assembly of the various parts of the grip assembly of the holder mechanism 59. The diameters of the respective bores through which the pin 54 passes are preferably dimensioned to permit the self-alignment rotation of the ring 57 and the relative movement of the tapered inserts 50 in a downward direction, as illustrated in FIG. 10, to increase the radial gripping force or thrust on the specimen end portion 55 as the tensile force is increased by the test apparatus.

In FIG. 11 there is shown an adaptor 60 in a modified holder mechanism 61. The adaptor 60 has a frusto-conical end portion 62 that is received in a generally frusto-conically shaped tapered seat 63 in a hemispherical ring 64. The ring 64 is in turn supported on a hemispherical seat 65 of a generally cup-shape holder 66 and the holder may in turn be coupled to a test apparatus in the manner described above, for example, with reference to FIG. 1. Inasmuch as the adaptor 60 may be formed of relatively hard material, for example, material similar to that of which the ring 64 is formed, the problem of inelastic deformation at the interface of the adaptor end portion 62 and the ring 64 at the seat 63 may be avoided so that the adaptor and ring may be relatively easily separated for disassembly of the holder mechanism 61 after testing.

The adaptor 60 has a coupling portion 67 outwardly of the holder 66 for coupling to a test specimen 69, which as illustrated, may consist of a pin 70 and clevis 71 arrangement, whereby the pin may be inserted in respective bores in the clevis and the specimen to couple the same. At the conclusion of a test operation the pin 70 may be removed to facilitate disassembly of the specimen 69 from the holder mechanism 61, and removal of the coupling portion 67 therefrom, as desired.

While the various parts of the test holder mechanism and particularly the hemispherical rings and inserts are normally made of metal, other materials such as ceramic materials having the requisite strength may be used to avoid any possible fusing of metals, facilitate easy separation and disassembly, etc.

From the foregoing, it will be apparent that the holder mechanism and, particularly, the test specimen grip assembly in accordance with the invention may be assembled and disassembled in a facile manner, assures firm gripping of the test specimen, and aids in self-alignment of the load train grip assembly during testing operations.

The embodiments of the invention in which an exclusive property or privilege is claimed are defined as follows:

1. An assembly for holding a test specimen in a test apparatus operative to apply a tensile force or the like to the specimen generally along an axis, comprising holder means for connecting an end portion of the specimen to the apparatus, said holder means including a body connectable to the test apparatus, a hemispherical seat in said body generally circumscribing such axis, and a hemispherical ring movably positioned on said hemispherical seat, said ring having an angularly tapered seat with respect to such axis, and plural insert means movably positioned on said angularly tapered seat for gripping the specimen end portion with an applied radial force that increases with an increase in the applied tensile force.

2. An assembly as set forth in claim 1, wherein said body is of generally cup shape with said hemispherical seat at one interior end thereof, and a central opening in said one interior end for extension of the specimen end portion into the interior of said cup shape body.

3. An assembly as set forth in claim 1, wherein each of said insert means has a tapered outer wall surface generally conforming to said angularly tapered seat in said ring.

4. An assembly as set forth in claim 3, wherein said angularly tapered seat and said angularly tapered outer wall surfaces of said insert means are generally of frusto-conical shape.

5. An assembly as set forth in claim 4, wherein each of said insert means is substantially identical.

6. An assembly as set forth in claim 4, wherein said outer wall surface of said insert means slidingly engages said angularly tapered seat in said ring for wedgingly gripping the specimen end portions.

7. An assembly as set forth in claim 6, wherein the specimen has a tapered end portion to be gripped by the assembly, and wherein said insert means includes an inner wall surface that is tapered generally to the same extent as the specimen end portion for firm wedge gripping of the same.

8. An assembly as set forth in claim 7, wherein the specimen tapered end portion is of frusto-conical shape and said inner wall surface of said insert means is of frusto-conical shape.

9. An assembly as set forth in claim 6, wherein said insert means includes a threaded inner wall surface for wedgingly gripping an end portion of a specimen.

10. An assembly as set forth in claim 6, wherein said insert means includes a serrated inner wall surface for directly abutting and wedgingly gripping the specimen end portion.

11. An assembly as set forth in claim 6, wherein said insert means includes an inner wall surface that extends generally parallel to such axis when said insert means is positioned on said angularly tapered seat for wedgingly gripping the specimen end portion.

12. An assembly as set forth in claim 11, wherein said inner wall surface is planar.

13. An assembly as set forth in claim 11, wherein said inner wall surface is planar and is generally of trapezoidal shape, and said insert means further includes land means bounding said inner wall surface.

14. An assembly as set forth in claim 6, further comprising pin means for connecting said holder means, said ring, said insert means and the specimen in operative assembled relation in the test apparatus while still permitting said insert means to grip the specimen end portion with an applied radial force that increases with an increase in the applied tensile force as aforesaid.

15. An assembly for holding a test specimen in a test apparatus operative to apply a tensile force to the specimen generally along an axis, comprising first and second holder means for holding the specimen in the apparatus, said first holder means including a body having an opening therethrough, and a self-aligning ring having an opening and positioned on said body with said openings generally in aligned relationship, an angularly tapered seat in said ring generally coextensive with said opening therethrough, and adaptor means for connecting said holder means and the specimen for application of tensile force to the latter by the test apparatus, said adaptor means including a seating portion firmly engageable with said angularly tapered seat, and coupling means extending through said openings beyond said holder means for mechanically coupling to the specimen.

16. An assembly as set forth in claim 15, wherein said coupling means comprises a pin and clevis connector.

17. An assembly for holding a test specimen in a test apparatus operative to apply a tensile force or the like to the specimen generally along an axis, comprising holder means for connecting an end portion of the specimen to the apparatus, said holder means including a body having an opening therethrough, a self-aligning ring having an opening and positioned on said body with said openings generally in aligned relationship, an angularly tapered seat in said ring generally coextensive with said opening therethrough, and plural insert means movably positioned on said seat for gripping the specimen end portion with an applied radial force that increases with an increase in the applied tensile force.

18. An assembly as set forth in claim 17, wherein there are two of said holder means for connecting the opposite end portions of the specimen to the apparatus.

* * * * *